United States Patent [19]

O'Keeffe

[11] Patent Number: 4,865,031
[45] Date of Patent: Sep. 12, 1989

[54] FABRIC AND METHOD OF USE FOR TREATMENT OF SCARS

[76] Inventor: Paul J. O'Keeffe, 1 Barana Parade, Roseville Chase, New South Wales, Austria

[21] Appl. No.: 253,953

[22] Filed: Oct. 3, 1988

Related U.S. Application Data

[63] Continuation of Ser. No. 883,148, Jul. 8, 1986, abandoned.

[30] Foreign Application Priority Data

Jul. 12, 1985 [AU] Australia .............................. PH1446
Nov. 19, 1985 [AU] Australia .............................. PH3467

[51] Int. Cl.$^4$ ......................... A61B 17/04; A61L 17/00
[52] U.S. Cl. ............................... 128/334 R; 128/335.5
[58] Field of Search ............................ 128/334, 335.5; 128/156

[56] References Cited

U.S. PATENT DOCUMENTS

| | | | |
|---|---|---|---|
| 1,382,715 | 6/1921 | Davis | 128/335.5 |
| 2,193,188 | 3/1940 | Bradley | 128/335.5 |
| 3,040,551 | 6/1962 | Urlaub | 128/156 |
| 3,108,357 | 10/1963 | Liebig | 128/334 R |
| 3,124,136 | 3/1964 | Usher | 128/334 R |
| 3,232,291 | 2/1966 | Parker | 128/156 |
| 3,272,204 | 9/1966 | Artandi et al. | 128/334 R |
| 3,276,448 | 10/1966 | Kronenthal | 128/334 R |
| 3,376,869 | 4/1968 | Borysko | 128/334 R |
| 4,051,848 | 10/1977 | Levine | 128/156 |
| 4,360,015 | 11/1982 | Mayer | 128/156 |
| 4,452,245 | 6/1984 | Usher | 128/334 R |

Primary Examiner—Edward M. Coven
Assistant Examiner—Gary Jackson
Attorney, Agent, or Firm—Bryan, Cave, McPheeters & McRoberts

[57] ABSTRACT

The present invention discloses a mesh like fabric for implantation beneath or within the dermis to control formation of scar tissue; the fabric being aligned such that its axis having the greatest resistance to distension is aligned parallel to the predominant stresses to which a wound is thought to be subject these being principally parallel to the wound line; axes of the fabric having lesser resistances to distension serving to control other stresses within the dermis transverse to the predominant longitudinal stresses; the fabric being provided with a binder in order to maintain the mesh structure in a known pre-stressed orientation.

16 Claims, 2 Drawing Sheets

FABRIC AND METHOD OF USE FOR TREATMENT OF SCARS

This is a continuation of U.S. application Ser. No. 883,148, filed July 8, 1986, now abandoned.

This invention relates to a product for sub or intradermal implantation in order to stabilise a wound and prevent the formation of excessive unsightly scar tissue.

For a number of years implants in the form of mesh and otherwise have been used surgically to reinforce the area proximate a surgical or trauma wound with a view to such implant being invaded by natural tissue thereby effecting a strong union of the damaged tissue.

It has not however previously been appreciated that implants in the nature of meshes or composite structures including mesh could be utilised within or just under the dermis where not only a strong union of the damaged tissue is required but furthermore in many cases an appealing union must be effected without excessive unsightly scar tissue. Indeed it has previously been thought that the use of mesh type structures in sub-dermal and intra-dermal applications would not be appropriate as the invasion of the mesh by body tissue which ensures a strong union of the wound may simultaneously produce excessive unsightly scar tissue.

Accordingly the present invention seeks to provide a mesh for intra-dermal and sub-dermal use adapted to stabilize wound during the healing process and further adapted to minimize the formation of unsightly scar tissue.

In its simplest form the present invention discloses a soft fine bio-compatible longterm bio-degradable mesh-like fabric fixed by a temporary bio-compatible bio-degradable binder into a pre-stressed position such that initial resistance to distension along one axis of its surface to at least one other such (non parallel) axis is known; the binder being such that it loses its rigidity soon after but not immediately upon contact with body fluids.

According to a further aspect of the invention there is disclosed a method of sub-dermally or intradermally implanting a fabric to control formation of scar tissue comprising the steps of:

(a) Observing the orientation of the wound to be healed with respect to the structure of the surrounding dermis;

(b) Determining the predominant stresses to which the wound and adjacent tissue are subject;

(c) Selecting a sheet of flexible bio-compatible longterm bio-degradable mesh-like fabric characterised in that it is relatively non-distensible along the axis intended to be implanted parallel to the primary stress carrying axis within the dermis as compared with its distensibility along any axis intended to be aligned with lesser stress carrying axes within the dermis;

(d) Implanting the fabric into or just under the dermis so as to bridge the wound in such a manner that the fabric supports the wound thereby facilitating healing and acting as a conduit for stresses passing through the wound.

Figure 1:
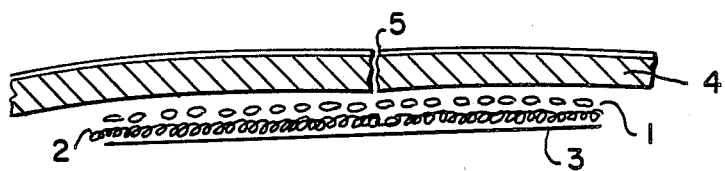
FIG. 1 is a cross-sectional view of a wound transverse to its longitudinal axis with sub-dermal installation of a fabric in accordance with the present invention.

According to FIG. 1 there is disclosed a composite fabric comprising layers 1, 2 and 3 in place beneath the dermis 4 spanning wound 5. The first layer 1 of the composite fabric is of a bio-degradable polymer fibre such as "white" silk which has been tricot knit and stretched.

The significance of the tricot knit is that the further it is stretched in one direction the more inextensible it becomes in that direction yet the more extensible it becomes in a direction perpendicular thereto. The fabric is placed so that the relatively inextensible axis lies parallel to the woundline which orientation has been found to avoid formation of excessive scar tissue. It is thought that the mechanism by which the fabric achieves this result is as follows.

The formation of scar tissue along the longitudinal axis of a wound is due to formation of a central core of fibres all arranged longitudinally along the wound and grouped into bundles. Whereas previously attempts to heal wounds without unsightly scar tissue have concentrated upon resisting stress forces transverse to the woundline it is proposed that the formation of unsightly longitudinal fibrous tissue is in response to stresses through the dermis parallel to the woundline. If an implanted fabric can resist these longitudinal stresses then it is considered that the signals which would otherwise be imparted to the scar tissue may be minimised thus reducing the scar's response; which is to produce further longitudinal fibres to thicken the scar into a "tendon like" structure.

The fact that the fabric is however extensible transverse to the woundline allows some degree of extension and contracture of the dermis along such axis and therefore stimulates formation of fibres in such transverse direction. The combined effect of the fabric is therefore to stimulate formation of a more uniform matrix of dermis fibres running both longitudinally and transversely of the wound rather than predominantly longitudinally.

The second component of the composite fabric comprises a lightly cross linked foamed gelatin 2. This layer of lightly cross linked foamed gelatin has been found to attract fibroblasts from the dermis and consequently enhance integration of the fabric into the fibre of the dermis. The fact that the lighly cross linked foamed gelatin 2 (e.g. "Gel Foam" TM British Pharmocapae) expands upon exposure to body fluids and tissue further mechanically assists the integration of the fabric into the dermis by urging same against the underside of the dermis.

Where the fabric is implanted sub-dermally as in FIG. 1 rather than intradermally the quantity of gelatin should be kept to the minimum required. The gelatin is used as a binder in order to stiffen the fabric and fix the yarn cross-over points into the pre-determined pre-stressed position. The fabric is therefore more readily handled by the surgeon as the gelatin will not relinguish its stiffening effect immediately upon contact with body fluids. The gelatin should however merely be a coating for the strands of the fabric rather than forming a solid sheet of matrix embedding the fabric. The gelatin may or may not be cross linked but if cross linked the cross linking should be minimal as the presence of a significant amount of strongly cross linked gelatin has been found to cause scar weakening after two or three weeks.

Unfortunately the fact that lightly cross linked foamed gelatin 2 swells on contact with tissue fluid means that installation of an implant merely comprising a fabric with a gelatin binder would be impeded by the tendency of the sheet to curl. To prevent this curling a thin layer of heavily cross linked gelatin 3 is incorporated into the composite fabric of FIG. 1 thus forming a sandwich with the fabric and heavily cross linked gelatin on either side of the lightly cross linked gelatin.

Figure 2:
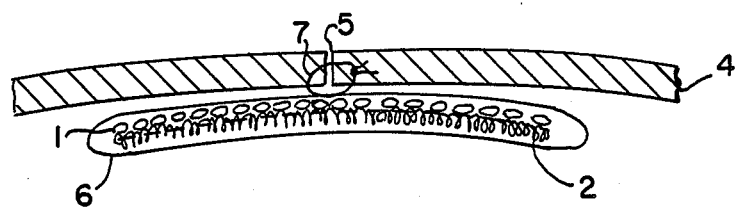
FIG. 2 is a cross-sectional view transverse to the woundline showing a further embodiment of the present invention utilising a sheath and applied sub-dermally.

With reference now to FIG. 2 there is disclosed an embodiment utilising a fabric 1 substantially as hereinbefore described with a layer of lightly cross linked foamed gelatin 2. Rather than incorporating a third layer of heavily cross linked gelatin to prevent curling as in the embodiment of FIG. 1 there is provided a waterproof relatively stiff transparent nylon sheath 6 in order to maintain the implant in a dry planar orientation until the plastic sheath is removed just prior to final closure of the wound.

Figure 5:
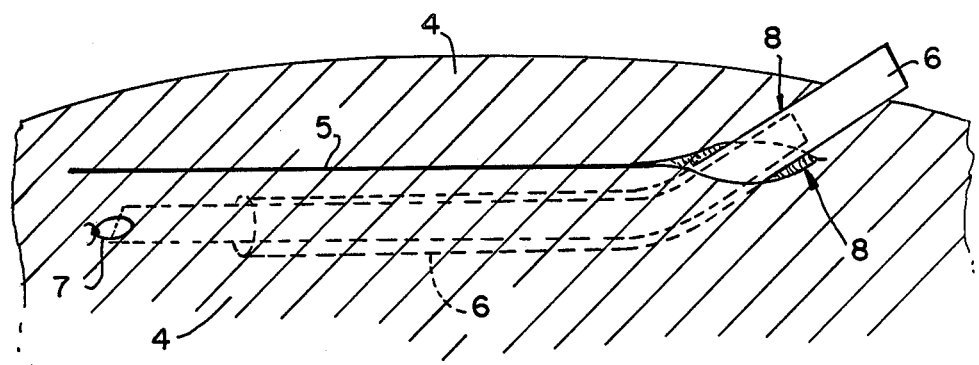
FIG. 5 is a perspective view of the embodiment of FIG. 4 during implantation intradermally along a wound.

FIG. 5 depicts s tubular plastic sheath just prior to removal and final closing of the wound. FIG. 5 depicts the fabric 1 affixed to the dermis 4 by suture 7 but with the sheath 6 not sutured to the dermis 4. When a sheath is utilised it is necesary that the sheath have some excess length over and above the required length of fabric in order that the wound 5 may be closed, except at one end, with the sheath still substantially surrounding the fabric. Before final closing the sheath will therefore protrude from one end of the wound as depicted in FIG. 5. The surgeon may then grasp the sheath adjacent end 8 in order to pull it substantially longitudinally of the wound thereby removing same from the dermis and from about the fabric. The fabric will remain in place within or beneath the dermis and if necessary the fabric may then be trimmed adjacent 8 in order to facilitate final closing of the wound with all of the fabric within or beneath the dermis.

Use of a sheath may be advantageous because it avoids the use of heavily cross linked gelatin which is removed from the body only very slowly by cellular activity.

It may be found desireable that where a sheath is incorporated with a fabric in accordance with the present invention a lubricant be incorporated between the fabric and the sheath particularly as gelatin tends to adhere to the sheath when body fluid enters the distal end of same during implantation. Vitamin E oil has been found useful as such a lubricant although any biocompatible oil would serve the purpose. Coating the fabric with an oil such as vitamin E gives an additional advantage in that the softening action exerted by body fluids on the binder will be retarded at least until the surgeon has completed the implant.

Figure 3:
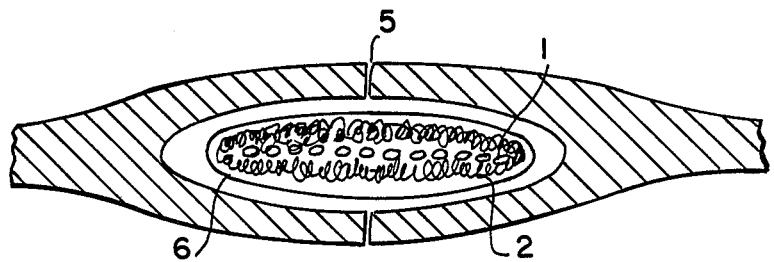
FIG. 3 is a cross-sectional view transverse to the woundline showing a further embodiment of the present invention utilising a sheath intradermally.

Turning now to FIG. 3 there is disclosed a further embodiment of the present invention utilising fabric 1 surrounded by lightly cross linked gelatin 2 and a sheath 6 but adapted to be affixed intradermally rather than sub-dermally. Intradermal application is preferred in most instances as sometimes a cleavage plane develops between the fabric and the underside of the dermis where sub-dermal implantation is utilised. Naturally in some areas such as the eyelids the dermis is not sufficiently deep in order to permit effective intradermal application and consequently sub-dermal application is preferred.

Figure 4:
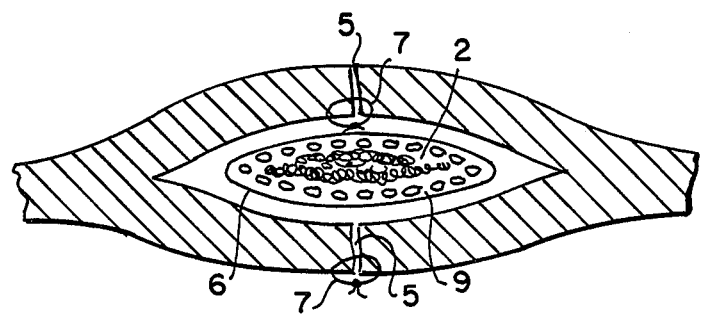
FIG. 4 is a cross-sectional view of an embodiment of the present invention utilising tubular fabric encased in a sheath and implanted intradermally.

FIG. 4 depicts an embodiment of the present invention specifically designed for intradermal use wherein the fabric is formed as a tricot knitted tube otherwise similar to that hereinbefore described. The tricot knitted tube envelops a core of lightly cross linked foamed gelatin 2 to assist with ingrowth of fibroblasts and furthermore to assist in urging the tubular mesh against the dermis. It will be appreciated that with intradermal application of this embodiment the gelatin cannot fail to urge the fabric against the dermis. A sheath 6 is utilised in this embodiment in order to assist handling as hereinbefore described.

One of the primary determinations to be made by a surgeon prior to use of a fabric in accordance with the present invention is the direction of the predominant stresses within the dermis surrounding the wound. If a surgeon is required to reduce an existing scar, then examination of existing scar tissue in accordance with the theory herein described should enable determination of the primary stresses affecting the scar as the thickening of the existing scar into tendon like collagen bundles is an indication that there are significant stresses parallel to such tendon like structures. A fabric should therefore be selected which will be relatively inextensible in a direction parallel to the predominant lines of stress as compared with other axes within the affected area.

Where a surgeon is not able to view an existing scar to determine the predominant stresses acting along a woundline, the surgeon may draw from experience with wounds on previous patients aligned in a similar manner and in the same area of the dermis as the patient to be treated.

In all events the applicant herein has determined that the longitudinal force acting along a woundline is always one of the principal stresses which requires a conduit if scar thickening is not to occur and consequently implanted fabric needs always to provide significant support along such axis.

Certain fabrics, if manufactured from non-distensible yarns will display virtually absolute non-distensibility along one axis with relative non-distensibility along an axis oblique thereto and perhaps significant distensibility perpendicular to such oblique axis. These three differing resistances to distension may be exploited in situations where for example a scar runs obliquely to skin creases. It is known that scars that run parallel to skin creases do well whereas scars perpendicular to skin creases do not do well. From this it should be assumed that support is required in a direction perpendicular to skin creases and consequently with an oblique scar one may align a fabric implant such that its absolute non distensibility corresponds with the direction of the woundline whereas the relatively non-distensible axis of the fabric runs transversly to the skin creases. The relatively distensible axis of the fabric may be aligned parallel to the skin creases.

Fabrics have been separately designed for either sub-dermal or intradermal implantation. Both fabrics are made from a material with an open weave. The degree of openness is based on the reticular pattern of the collagen bundles in the deeper layer of the dermis. This can be seen when a skin graft is harvested from a donor site. The pattern of fibres in the donor site is similar to the pattern of a coarse bridal veil material (tulle).

Another factor determining the thickness of yarn and openness of the fabric is the realisation that the fabric must allow speedy ingrowth of fibrocellular tissue for adequate anchoring of the fabric to the dermis. The yarn must be large enough to withstand tissue tensions without breaking and not so small that it will cut through the tissue when under tension. The bulk of implanted material must not be so great as to produce excess foreign body reactions.

Essentially the fabric is designed to manage the tissue stress in the scar and adjacent skin and to provide a template to induce the formation of a balanced collagen matrix around the scar akin to that of normal tissue. Normal tissue displays a matrix of collagen bundles running in differing directions whereas scar tissue is a result of formation of excessive bundles of uni-directional collagen.

The term "longterm bio-degradable" where used herein shall mean bio-degradable within 1–5 years. Dated this 3rd day of July, 1986. DR. PAUL JOHN O'KEEFFE The claims defining the invention are as follows:

1. A soft, fine, bio-compatible, long term bio-degradable mesh-like fabric fixed by a bio-compatible binder in a pre-stressed state such that the fabric is relatively resistant to distension along one axis of its surface as compared to at least one other such non parallel axis; wherein the binder is adapted to lose its rigidity soon after, but not immediately upon, contact with body fluids.

2. A fabric as claimed in claim 1 manufactured from long-term biodegradable silk thread of between 0.009 mm to 0.2 mm diameter.

3. A fabric as claimed in claim 1 being formed as a tulle having apertures of between 0.01 mm and 5 mm wide.

4. A fabric as claimed in claim 1 being tricot knit with apertures of between 0.01 and 0.5 mm wide.

5. A fabric as claimed in claim 1 wherein the binder is a light coating of dried gelatin or collagen.

6. A fabric as claimed in claim 1 wherein the binder is a light coating of gelatin or collagen, the gelatin or collagen being cross linked to the extent that the binder maintains its rigidity at least until the fabric is implanted and the action of body fluids on the binder softens the binder.

7. A fabric as claimed in claim 1 wherein the gelatin binder is applied to one side only of the fabric and an additional layer of more heavily cross linked gelatin is applied over the binder in order to prevent curling of the fabric when it is applied sub-dermally, the extent of cross linking of the additional layer being adequate to resist immediate expansion of the binder upon exposure to body fluids.

8. A fabric in accordance with claim 1 wherein there are provided two layers of fabric with a binder of gelatin or collagen; the binder being predominantly disposed between the two layers of fabric and cross linked to the extent that when used intradermally, contact between body fluids and the binder causes expansion in the binder which urges each layer of fabric against the dermis; the binder serving to attract fibroblasts from the dermis through each layer of fabric.

9. A fabric in accordance with claim 1 wherein the configuration of the fabric is a flattened tube with a binder of gelatin or collagen, the binder being predominantly disposed within the tubular structure and cross linked to the extent that when used intradermally, contact between body fluids and the binder causes expansion of the binder which urges the fabric against the dermis, the binder serving to attract fibroblasts from the dermis through each layer of fabric.

10. A fabric in accordance with claim 1 hereof wherein the fabric/binder unit is coated with an oil in order to retard the softening action exerted by the body fluids on the binder at least until the surgeon has completed the implant.

11. A fabric in accordance with claim 1 hereof wherein the fabric/binder unit is coated with vitamin E oil in order to retard the softening action exerted by the body fluids on the binder at least until the surgeon has completed the implant.

12. A fabric in accordance with claim 1 in combination with a sheath, wherein the fabric is incorporated in the sheath which is adapted to be temporarily partially implanted in a wound; the sheath being sufficiently rigid to prevent curling, buckling or bunching of the fabric; and the sheath being adapted to prevent contact between body fluids and at least a substantial portion of the fabric and adapted for removal from about the fabric prior to closing of the wound.

13. A fabric in accordance with claim 1 in combination with a sheath, wherein the fabric is incorporated in the sheath which is adapted to be temporarily partially implanted in a wound; the sheath being sufficiently rigid to prevent curling, buckling or bunching of the fabric; the sheath adapted to prevent contact between body fluids and at least a substantial portion of the fabric and adapted for removal from about the fabric prior to closing of the wound; a bio-compatible oil being interposed between the fabric and the sheath as a lubricant to assist removal of the sheath from about the fabric.

14. A fabric in accordance with claim 1 in combination with a sheath, wherein the fabric is incorporated in a stiff nylon transparent sheath; the sheath being sufficiently rigid to prevent curling, buckling or bunching of the fabric; the sheath adapted to prevent contact between body fluids and at least a substantial portion of the fabric and adapted for removal from about the fabric prior to the closing of the wound.

15. A fabric in accordance with claim 13 wherein the bio-compatible oil is Vitamin E oil.

16. A method for sub-dermally or intradermally implanting a fabric to control formation of scar tissue which comprises implanting a bio-compatible, long-term bio-degradable mesh-like fabric which is fixed by a temporary bio-compatible binder in a pre-stressed state, said fabric being non-distensible along one axis as compared with its distensibility along at least one other non-parallel axis, into or just under the dermis proximate the wound in such a manner that the relatively non-distensible axis of the fabric is parallel to the suspected primary stress carrying axis within the dermis.

* * * * *